(12) United States Patent
Lai

(10) Patent No.: US 8,486,460 B2
(45) Date of Patent: Jul. 16, 2013

(54) HERBAL COMPOSITION FOR LOWERING LIKELIHOOD OF STROKE AND METHODS FOR HEALING STROKE PATIENTS

(76) Inventor: Katharine Lai, West Orange, NJ (US)

( * ) Notice: Subject to any disclaimer, the term of this patent is extended or adjusted under 35 U.S.C. 154(b) by 0 days.

(21) Appl. No.: 13/373,202

(22) Filed: Nov. 8, 2011

(65) Prior Publication Data

US 2013/0115319 A1    May 9, 2013

(51) Int. Cl.
*A61K 36/00* (2006.01)
*A61K 36/16* (2006.01)
*A61K 36/236* (2006.01)
*A61K 36/287* (2006.01)
*A61K 36/60* (2006.01)

(52) U.S. Cl.
USPC .......................... 424/725; 424/757; 424/752

(58) Field of Classification Search
None
See application file for complete search history.

*Primary Examiner* — Qiuwen Mi

(57) ABSTRACT

Compositions and methods are provided for lowering blood pressure, lowering blood sugar, lowering cholesterol, prevent stroke, removing age spots, curing stroke, or enlarging blood vessels to remove the toxins from the blood. In one embodiment, the composition comprises the herbal extracts of liquorice root, self-heal, mulberry leaves, chrysanthemum, ginkgo nuts, mangosteen, maltose and dextrin. The composition is used as a nutraceutical treatment to lower likelihood of stroke.

4 Claims, 2 Drawing Sheets

HERBAL COMPOSITION FOR LOWERING LIKELIHOOD OF STROKE AND METHODS FOR HEALING STROKE PATIENTS

FIELD OF THE INVENTION

The present disclosure relates broadly to herbal supplement and, more particularly relates to herbal supplements to reduce a likelihood of stroke and methods for delivery of the same.

BACKGROUND OF THE INVENTION

Some people based on physical features or genetic disposition are more likely than the general population to suffer a debilitating stroke.

A stroke, previously known medically as a cerebrovascular accident (CVA), is the rapidly developing loss of brain function(s) due to disturbance in the blood supply to the brain. This can be due to ischemia (lack of blood flow) caused by blockage (thrombosis, arterial embolism), or a hemorrhage (leakage of blood). As a result, the affected area of the brain is unable to function, which might result in an inability to move one or more limbs on one side of the body, inability to understand or formulate speech, or an inability to see one side of the visual field.

A stroke is a medical emergency and can cause permanent neurological damage, complications, and death. It is the leading cause of adult disability in the United States and Europe and the second leading cause of death worldwide. Risk factors for stroke include old age, hypertension (high blood pressure), previous stroke or transient ischemic attack (TIA), diabetes, high cholesterol, cigarette smoking and atrial fibrillation. High blood pressure is the most important modifiable risk factor of stroke.

The lack of effective and widely applicable pharmacological treatments for stroke patients may explain a growing interest in traditional medicines, for which extensive observational and anecdotal experience has accumulated over the past thousand years. The World Health Organization (WHO) defines traditional medicine as "health practices, approaches, knowledge and beliefs incorporating plant, animal and mineral based medicines, spiritual therapies, manual techniques and exercises, applied singularly or in combination to treat, diagnose and prevent illnesses or maintain well-being". Unlike Western medicine, which focuses on disease, traditional medicine takes the approach that the body provides external clues to an internal imbalance that can be addressed by interventions such as herbs and acupuncture (holistic treatment approach).

Thus, there is a heightened need for alternative herbal supplements that may prevent and cure strokes.

SUMMARY OF THE INVENTION

The present disclosure provides novel compositions and methods for nutraceutical use in a mammal, preferably in a human.

The present disclosure is divested to a novel composition of liquorice root, self-heal, mulberry leaves, chrysanthemum, ginkgo nuts, mangosteen, maltose and dextrin, wherein ginkgo nuts is processed to remove the fruit toxins.

The present disclosure provides a method for lowering blood pressure, lowering blood sugar, lowering cholesterol, prevent stroke, removing age spots or enlarging blood vessels to remove the toxins from the blood vessel in the body of a mammal in need thereof, comprising: administering to the mammal in need thereof an effective amount of the composition which comprises liquorice root, self-heal, mulberry leaves; chrysanthemum, ginkgo nuts, mangosteen, maltose and dextrin.

The present disclosure provides a method for curing stroke in a mammal in need thereof comprising: administering to the mammal in need thereof an effective amount of the composition which comprises liquorice root, self-heal, mulberry leaves; chrysanthemum, ginkgo nuts, mangosteen, maltose and dextrin.

BRIEF DESCRIPTION OF THE DRAWINGS

The present disclosure can best be understood in connection with the accompanying drawings. It is noted that the disclosure is not limited to the precise embodiments shown in drawings, in which.

DETAILED DESCRIPTION OF THE INVENTION

The present disclosure provides novel compositions and methods for nutraceutical use in a mammal, preferably in a human.

In one aspect, compositions are provided which comprise an herbal extract of liquorice root, self-heal, mulberry leaves, chrysanthemum, ginkgo nuts, mangosteen, maltose and dextrin. The combination of these herbal extracts may enhance their functions compared to that when administered alone. Therefore, the combination synergizes the activity of the herbal extracts.

Figure 1:
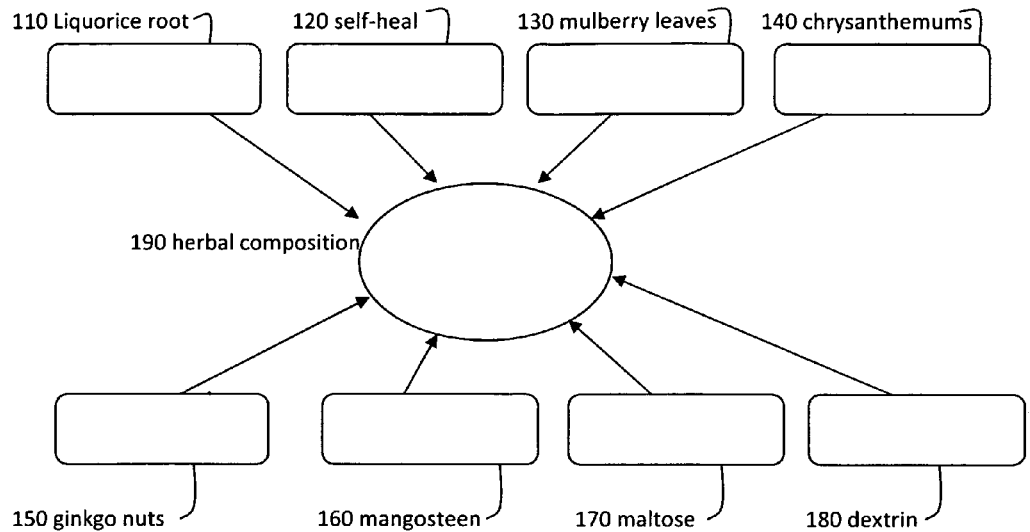
FIG. 1 shows the herbal ingredients and its composition.

With reference to the drawings, and in particular to FIG. 1 where illustrates the herbal composition 190 and all the herbal ingredients: liquorice root 110, self-heal 120, mulberry leaves 130, chrysanthemum 140, ginkgo nuts 150, mangosteen 160, maltose 170 and dextrin 180.

The following is a detailed description of example embodiments of the disclosure depicted in the accompanying drawings. The example embodiments are in such detail as to clearly communicate the disclosure and are designed to make such embodiments obvious to a person of ordinary skill in the art. However, the amount of detail offered is not intended to limit the anticipated variations of embodiments; on the contrary, the intention is to cover all modifications, equivalents, and alternatives falling within the spirit and scope of the present disclosure, as defined by the appended claims.

In some embodiments, the herbal components of the composition contain minimal amounts of water. In some embodiments the herbal components contain less than 0.5% of water by weight. In other embodiments, the herbal components of the composition contain less than 0.1% water by weight.

For oral administration, the compositions may optionally be formulated by mixing the herbal ingredients in combination with physiologically or pharmaceutically acceptable carriers that are well known in the art. Such carriers enable the herbal ingredients to be formulated as sealable tea bags, tablets, pills, capsules, emulsions, lipophilic and hydrophilic suspensions, liquids, gels, syrups, slurries, suspensions and the like, for oral ingestion by an individual or a patient to be treated.

Figure 2:
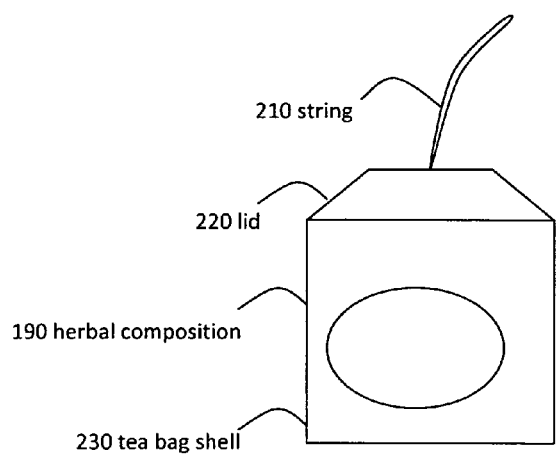
FIG. 2 shows the composition formulated into a sealable tea bag.

FIG. 2 illustrates a tea bag where shows the herbal composition 190 and string 210, bag lid 220 and tea bag shell 230.

Figure 3:
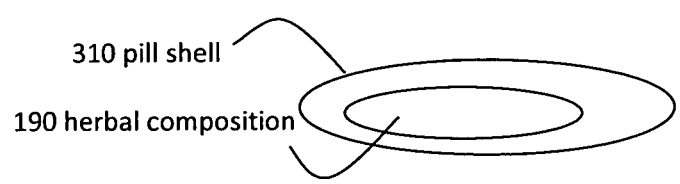
FIG. 3 shows the composition formulated into a pill.

FIG. 3 illustrates a pill shape carrier with the herbal composition 190, and pill shell 310.

Each dosage unit contains about 10 g of a mixture of herbal extracts of liquorice root, self-heal, mulberry leaves, chrysanthemum, ginkgo nuts, mangosteen, maltose and dextrin.

In another aspect of the disclosure, a method of lowering blood pressure, lowering blood sugar, lowering cholesterol, preventing stroke, and removing age spots is provided. The method of lowering blood pressure, lowering blood sugar, lowering cholesterol, preventing stroke, and removing age spots comprises administering to a mammal in need thereof, an effective amount of any of the compositions described above. The mammal is preferably a human.

In yet another aspect of the disclosure, a method of curing stroke is provided. The method comprises administering to a mammal in need thereof an effective amount of any of the compositions described above. The mammal is preferably a human. By administering a composition of the disclosure, stroke is cured.

In the methods of the present disclosure, a composition is administered orally. The amount of the composition administered will be dependent on the subject being treated, the subject's weight, the manner of administration, the judgment of the prescribing physician and/or the origins where the ingredients come from. It makes a difference in the ratio whether the herbs grow in the northern part or the southern part of the world.

In some embodiments, the compositions are administrated as tea bags two or three times a day. In some embodiments, more than one tea bag is administered at the same time. In some embodiments, the compositions are administered as pills two or three times a day. In some embodiments, more than one pill is administered at the same time. In some embodiments, the compositions are administered as capsules two or three times a day. In some embodiments, more than one capsule is administered at the same time. In some embodiments, the compositions are administered as liquid doses two or three times a day. In some embodiments, more than one liquid dose is administered at the same time.

In some embodiments of the disclosure, the composition is administered to a human at a dose of about 1-60 g/day, more preferably about 60-90 g/day, even more preferably about 90 g/day.

For example, to cure stroke, the dosage of the composition is about 10 g, three dosages for three times a day. In some embodiments of the methods of the disclosure, the composition is administered to a mammal at a dose of about 1-20 g three times a day. In other embodiments of the methods of the disclosure, the composition is administered to a mammal at a dose of about 20-30 g three times a day.

In the foregoing description, certain terms and visual depictions are used to illustrate the preferred embodiment. However, no unnecessary limitations are to be construed by the terms used or illustrations depicted, beyond what is shown in the prior art, since the terms and illustrations are exemplary only, and are not meant to limit the scope of the present.

It is further known that other modifications may be made to the present disclosure, without departing the scope of the disclosure, as noted in the appended Claims.

What is claimed is:

1. A method for treating stroke in a mammal in need thereof comprising: administering to the mammal in need thereof an effective amount of the composition which comprises liquorice root, self-heal, mulberry leaves; chrysanthemum, ginkgo nuts, mangosteen, maltose and dextrin.

2. The method of claim 1, wherein said administration is oral.

3. The method of claim 1, wherein the composition is administered to a human at a dose of about 90 g/day.

4. The method of claim 1, wherein the composition is orally administrated to a human at a dose of about 30 g three times a day.

* * * * *